(12) United States Patent
Anvar et al.

(10) Patent No.: US 7,393,693 B2
(45) Date of Patent: Jul. 1, 2008

(54) METHODS AND PROCEDURES FOR STABILIZATION AND PERFORMANCE OPTIMIZATION OF MULTI-LAYER SOL-GEL CHEMICAL AND BIOCHEMICAL SENSORS

(75) Inventors: David J. Anvar, Mountain View, CA (US); Ganapati R. Mauze, Sunnyvale, CA (US); Dan-Hui Yang, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 592 days.

(21) Appl. No.: 10/159,301

(22) Filed: May 31, 2002

(65) Prior Publication Data

US 2003/0224530 A1    Dec. 4, 2003

(51) Int. Cl.
*G01N 30/00* (2006.01)
(52) U.S. Cl. .................... 436/176; 422/50; 422/55; 422/56; 422/57; 422/68.1; 436/73; 436/22
(58) Field of Classification Search ............... 422/50, 422/55, 56, 57, 68.1, 99; 436/528, 73, 22, 436/176, 72
See application file for complete search history.

(56) References Cited

U.S. PATENT DOCUMENTS 5,344,703 A * 9/1994 Kovar et al. ............... 428/312.6
5,501,836 A    3/1996 Myerson
5,608,006 A    3/1997 Myerson
5,942,189 A    8/1999 Wolfbeis et al.
6,022,748 A    2/2000 Charych et al.
6,046,055 A    4/2000 Wolfbeis et al.
6,299,596 B1 * 10/2001 Ding .................. 604/96.01

OTHER PUBLICATIONS

C. Rottman et al., "Doped sol-gel glasses as pH sensors," Materials Letters 13 (1992), 293-298.

* cited by examiner

*Primary Examiner*—Jill Warden
*Assistant Examiner*—Samuel P Siefke

(57) ABSTRACT

A sensor and method for making a sensor includes providing a substrate having an adhesion layer with a first functional group operatively associated with a sol-gel composition having a second functional group, and at least one linker material for connecting the first functional group to the second functional group. In another embodiment, a sensor and method for making the sensor includes providing a sol-gel layer operatively associated with a sol-gel precursor solution that includes at least one co-polymer and at least one solvent adapted to resist the deformation of the sol-gel layer by decreasing evaporation, decreasing cross-linking, increasing intermolecular forces, or increasing elasticity.

19 Claims, 1 Drawing Sheet

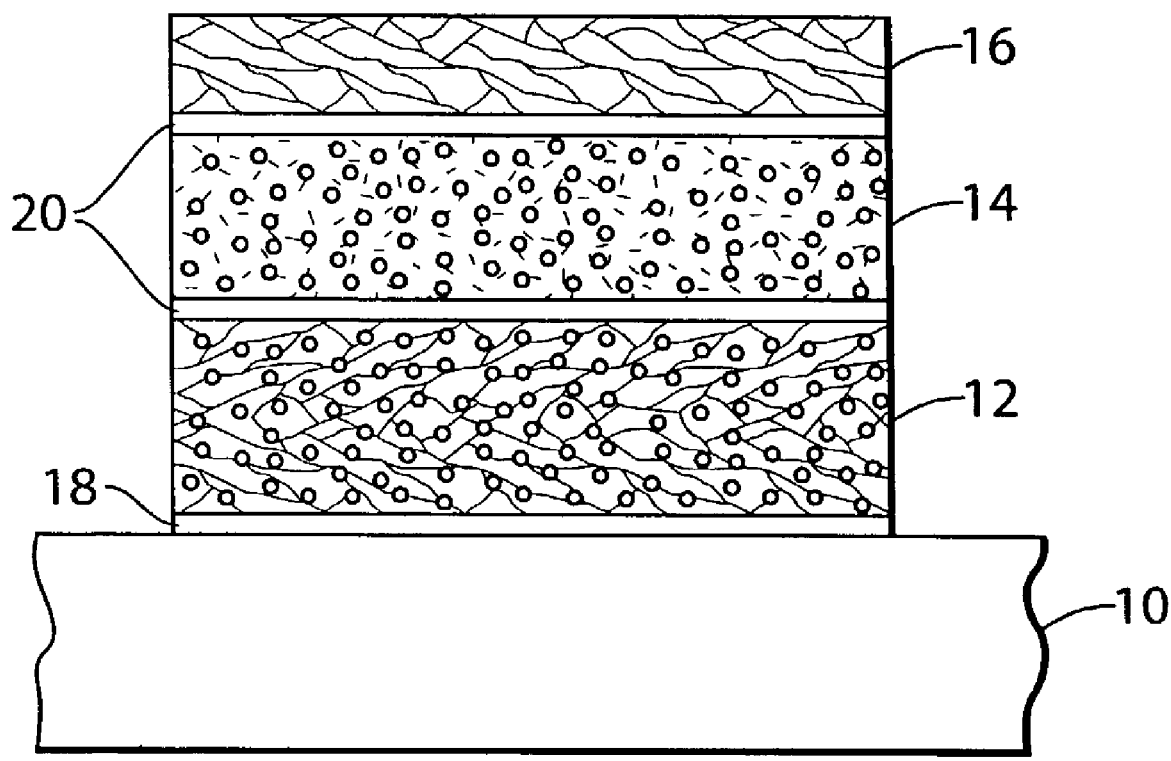
Figure

METHODS AND PROCEDURES FOR STABILIZATION AND PERFORMANCE OPTIMIZATION OF MULTI-LAYER SOL-GEL CHEMICAL AND BIOCHEMICAL SENSORS

BACKGROUND OF THE INVENTION

Field of the Invention

The present invention relates to chemical sensors as seen in diagnostic sensing and high-throughput drug screening using sensing material immobilized on sol-gels. More particularly, the invention relates to stabilizing and optimizing multi-layer sol-gel chemical and biochemical sensors.

Sol-gel glasses have been used as a basis for chemical and biochemical sensors. Sol-gel glass is an optically transparent amorphous silica or silicate material produced by forming interconnections in a network of colloidal, sub-micron particles under increasing viscosity until the network becomes completely rigid, with about one-half the density of glass. Sol-gel copolymers are sol-gel polymers produced by the simultaneous polymerization of two or more dissimilar monomers using the sol-gel process.

SUMMARY OF THE INVENTION

The present invention relates to preventing or minimizing deformation of sol-gel layers in a sol-gel chemical and biochemical sensor.

BRIEF DESCRIPTION OF THE DRAWING

The invention will become more apparent from the following detailed specification and drawing in which:

FIG. 1 shows an embodiment of the claimed invention, wherein the sensor has three layers.

DETAILED DESCRIPTION OF THE INVENTION

It is noted that, as used in this written description and the appended claims, the singular forms of "a," "an," and "the" include plural referents unless expressly and unequivocally limited to one referent. Thus for example, reference to "a sol-gel" includes mixtures of two or more sol-gels, whereas reference to "R is chosen from a hydrogen atom, an alkyl radical, and an alkoxy radical" is limited to one substitute for R.

The sol-gel process comprises forming glass at low temperatures from starting monomers or precursors by chemical polymerization in a liquid phase; a gel is formed from which glass can be derived (i.e., a sol-gel glass) by the successive elimination of the liquid phase such as water generated by condensation reactions. In one embodiment, the sol-gel process uses hydrolysis and condensation of the starting monomers to produce a colloidal suspension (the "sol"), gelation (to form a porous matrix), and drying (and shrinking) to form the "gel." In one embodiment, sintering at elevated temperatures makes the gel more dense to form a pore-free glass. In one embodiment, the sol-gel process begins with soluble ingredients. Usually, these are organic silicates such as tetramethoxysilane (TMOS) or tetraethoxysilane (TEOS), which react with water and alcohol to form extremely small colloidal structures that comprise the sol. While mixing the liquid ingredients with the water and alcohol, a hydrolysis reaction occurs. The hydrated silica immediately interacts in a condensation reaction forming Si—O—Si bonds.

Linkage of additional Si—OH tetrahedra occurs as a polycondensation reaction, eventually resulting in a $SiO_2$ network. Hydrolysis and polycondensation reactions initiate at numerous sites within the TMOS or TEOS aqueous solution as mixing occurs. It is in this TMOS or TEOS aqueous solution that sol-gel precursors which form bonds with sensing material may be added. The term "sol-gel precursor" refers to any material added to the sol-gel composition for the purpose of maintaining the integrity of the sol-gel. Sol-gel precursors include but are not limited to organic silicates and functionalized silica alkoxides. In one embodiment, the sol-gel precursor can be at least one monomeric orthosilicate. The hydrolysis and polycondensation reactions also operate on these precursors. When sufficient interconnected Si—O—Si bonds are formed in a region they respond cooperatively as a colloidal (submicron) particle, or pre-network. The sol becomes the suspension of these colloidal particles in their parent liquid. The sol still behaves as a low-viscosity liquid and can be cast into a mold.

After casting into a mold, gelation occurs: the colloidal particles link together to become a three-dimensional matrix. When gelation occurs, viscosity increases sharply and a solid results. Aging of a gel involves keeping the gel immersed for some period of time (hours to days), during which time the gel decreases in porosity and develops the necessary strength. The term "sol-gel composition" refers to the materials necessary to compose a sol-gel as described above, any sensing material incorporated into the sol-gel, and any other additives incorporated into the sol-gel to alter the properties of the sol-gel.

The sol-gel glass can be optically transparent but contains a large fraction of interconnected pores. Analyte sensing compounds of various kinds can be incorporated into the porous matrix during the formation of the sol-gel. The properties of the sol-gel depend on the sol-gel precursor used, the pH of the sol-gel precursor solution, concentration of additives, the water concentration and temperature. The sol-gel technique has also been shown as a way to immobilize sensing material. Analyte sensing compounds can be immobilized by entrapping or caging them in the porous matrix during formation of the sol-gel. The analyte sensing compound remains active and relatively stationary, being physically trapped or entangled in the three-dimensional silica structure created during the sol-gel process.

Sensors, in order to be reliable, reproducible and practical, usually require that whatever sensing sol-gel layers (i.e. those that contain analyte sensing compounds) are incorporated in the sensor do not become detached from the substrate. The term "sensor" refers to any chemical or biological sensitive structure comprising a composition or component adapted to detect or measure an analyte or material of interest. A sensor can comprise a substrate, sol-gel layer, diffusion control layer, adhesion layer, any other chemical or mechanical structure used in the sensor configuration, or any combination thereof. A sensor can be adapted to electrical, optical, and/or mechanical signal coupling with a signal transducer to capture the signal for such detection or measurement.

Delamination or detachment of the entire sensing sol-gel layer from the substrate can affect the performance of the sensor by degradation of signal coupling (i.e. the amount of signal reaching its destination), such as electrical, optical, or mechanical signal coupling, between the sensor and the signal transducer. In addition, adjacent sensing sol-gel layers can require some interfacial control to mitigate transmission of byproducts and resistance to transmitting analytes across the interface between the adjacent layers. Further problems include shrinking and/or cracking of sensing layers following deposition or molding, and uncontrolled analyte diffusion regardless of analyte concentration.

The present invention relates to preventing or minimizing deformation of sol-gel layers in a sensor. The term "deformation" refers to detachment, shrinking, cracking of the sol-gel to disrupt the interface between said sol-gel and another sol-gel, substrate or diffusion control layer. FIG. 1 illustrates one embodiment of a sensor.

In one embodiment, the sensor has three layers as shown in FIG. 1. The substrate (10) has a first sol-gel layer (12) deposed on it, then a second sol-gel layer (14) deposed on the first sol-gel layer (12), and finally a diffusion control layer (16) deposed on the second sol-gel layer (14). The adhesion of sol-gel layers to the substrate can be promoted by an adhesion layer (18) that contains linker molecules (e.g. glutaraldehyde) which connect functional groups in between the substrate (10) and the first sol-gel layer (12). The adhesion of sol-gel layers can be promoted by an adhesion layer (20) between the first sol-gel layer (12) and the second sol-gel layer (14), and between the second sol-gel layer (14) and the diffusion control layer (16). The diffusion control layer (16) can be made of sol-gel or other material adapted to control the diffusion of desired material into the underlying sol-gel layers.

In other embodiments, the sensor can have any number of layers, including any combination of sol-gel layers and diffusion control layers adhered together with an adhesion layer. The term "adhesion layer" refers to any thin film or monolayer adapted to maintaining the contact or promote adhesion between the one sol-gel layer and another sol-gel layer, or a sol-gel and a substrate.

In another embodiment (not pictured), first sol-gel layer (12), second sol-gel layer (14), and diffusion control layer (16) can be modified by treatment during formation or surface treatment after formation with mobile (i.e. free to move throughout the bulk matrix) or attached (i.e. stationary in the matrix structure) materials to allow first sol-gel layer (12) to adhere to substrate (10) without adhesion layer (18), and allow second sol-gel layer (14) to adhere to diffusion control layer (16) and first sol-gel layer (12) without adhesion layer (20). The term "adhere" or "adhesion" refers to any chemical force attaching two layers together including coattachment, covalent bonding, polar bonding, and other means to maintaining two layers in contact. As referred to above, an adhesion layer allows adhesion of two layers that would not adhere sufficiently for the particular application such as a chemical sensor.

The term "substrate" refers to the portion of the sensor which consists of any support whether glass based or polymer based on which the sol-gel layers and diffusion controlling layers can be deposited. The adhesion between a substrate and a sol-gel can be affected by the nature of the substrate. Many substrates are known in the art of chemical and biochemical sensors that can act as support to sol-gels for electrical, optical, and/or mechanical signal coupling between sensor and the signal transducer.

In one embodiment, the substrate comprises glass. An adhesion layer is applied to the glass substrate surface. The adhesion layer adheres or bonds to the substrate. The adhesion layer also comprises material with a first functional group. The sol-gel comprises a second functional group. The adhesion layer also comprise a linker material adapted to connect the first functional group to the second functional group.

In one embodiment, the adhesion layer comprises 3-aminopropyltriethoxysilane (Sigma-Aldrich Corp., St. Louis, Mo., A3648, 919-30-2) (hereinafter "APES"). The APES adheres to the glass substrate, and provides an amino group to serve as the first functional group. The sol-gel is formulated from precursors comprising aminotrimethoxysilane (Amino-Tri-MOS). The Amino-Tri-MOS provides an amino group to serve as the second functional group. The linker material comprises glutaraldehyde to link the amino groups of APES and Amino-Tri-MOS.

In another embodiment, the sol-gel can contain 3-mercaptopropyltrimethoxysilane (Power Chemical Co., China, PC2300) (hereinafter "MPS"). The MPS adheres to the glass substrate, and provides a mercapto group to serve as the first functional group. The sol-gel is formulated from precursors comprising metals with mercapto groups to serve as the second functional group. The linker material is adapted to facilitate the formation of metal sulfur bonds or disulfide bonds. An example of metal used for such purposes is gold.

In another embodiment, protein chemistry can be used to facilitate adhesion, by using functionalized proteins known in the art of protein chemistry such as sulfur-peptide bonds.

The method for making an embodiment of the sensor comprises applying an adhesion layer with a first functional group to a substrate, mixing a second functional group into a sol-gel, either condensing or co-condensing the second functional group in the sol-gel, treating the substrate covered with an adhesion layer with a linker material solution, and depositing the sol-gel with the condensed second functional group on the substrate so that the linker material can connect the first functional group on the adhesion layer to the second functional group in the sol-gel. In one embodiment, the method can depose an APES adhesion layer, where the first functional group is an amino group and the second functional group is also amino group based on an amino functionalized sol-gel. The linker material in this embodiment can be glutaraldehyde which is adapted to link the two amino groups from the first and second functional groups.

In one embodiment, the substrate can be treated by a variety of processes including plasma treatment, corona discharge, and substrate specific reactions to promote adhesion between the sol-gel and substrate. In a polymer substrate embodiment, these reactions can oxidize the polymer surface. The term "substrate-specific reactions" refers to any wet or gaseous chemistry including but not limited to oxidation, reduction, addition, elimination, diffusive doping, and other reactions known in the art for their ability to treat the surface of a substrate. In another embodiment, the substrate treatment can comprise conjugation reactions with the treated surface. The term "conjugation reactions" refers to any reaction which joins the substrate with any other material, including attaching material onto the substrate's treated surface.

In one embodiment, while improving the mechanical adhesion, as described above, the optical quality of the sol-gel/substrate interface can be altered. Prior to alteration, the substrate can have a first refractive index, and the sol-gel can have a second refractive index. During the process, the second refractive index of the sol-gel can be made substantially similar to the first refractive index of the substrate. In one embodiment, this can be done by varying (i.e. reducing or increasing) the ratio of a variety of monomeric orthosilicates or additives known in the art to alter the refractive index of the resulting gel. In one embodiment, this can be done by manipulating (i.e. altering the reaction condition such as temperature and concentration) the condensation kinetics of the sol-gel precursors to vary the second refractive index in the sol-gel.

In one embodiment, while improving the mechanical adhesion, as described above, the selectivity of reactions between analyte species diffusing through the sol-gel pores and sensing material immobilized within the sol-gel matrix can be altered. The term "selectivity" refers to the ability to control reactions in the sol-gel by limiting what material penetrates into the sol-gel. In one embodiment, the selectivity of electrode reactions in a sensor (i.e. an electrochemical sensor) can be controlled by changing the properties of the access holes (those pores which are in contact with the surface of the sensor) on the sensor (i.e. electrode) surface. These access holes give the sol-gel its porosity based on different condensation conditions (e.g. temperature and concentration of sol-gel precursors). In one embodiment, the size of the access holes can be changed by controlling the hydrolysis kinetics (e.g. the rate of drying the sol-gel). In another embodiment, the polarity of the access holes can be changed by addition of polar constituents to the sol-gel matrix. In another embodiment, the chemical affinity of the access holes can be changed by addition of chemically reactive constituents to the sol-gel matrix.

In one embodiment, the sol-gel can be treated by a variety of adhesion compositions to promote adhesion between the one sol-gel layer and another sol-gel layer. To create an adhesion layer it is necessary to change the chemical nature of the sol-gel surface. To do so, the sol-gel can be subjected to general treatment, for example with gaseous plasma or gaseous corona discharge, or selective treatment, for example with room temperature (20° C.) liquid chlorosilanes, room temperature (20° C.) liquid orthosilicates, volatile chlorosilane, glutaraldehyde, or sol-gel precursors, or combinations of general and selective treatments. The examples discussed below illustrate both gaseous plasma for general treatment and wet chemical oxidation of a vinyl group to an alcohol or aldehyde for a selective treatment.

In one embodiment, the first and second sol-gel layers can either have similar or different compositions. The second sol-gel layer can be at least partially treated with an adhesion layer leaving areas on the sol-gel untreated. Vapor or gaseous treatment, as in the embodiments which treat with compositions comprising volatile chlorosilane or glutaraldehyde, exhibit the desirable characteristics for a probe, dopant, or reagent material in the bulk phase (i.e. mobile throughout the sol-gel matrix) or in the second sol-gel matrix where the first sol-gel is reactive to the solvent solution comprising the probe, dopant, or reagent material. This allows treating different sensors independently where multiple sensors are deposited as in a micro-array.

Promoting adhesion at the interface can facilitate the deposition of sol-gel layers which comprise incompatible polymers and/or have chemistries that render the sol-gel layers incompatible with each other. The presence of adhesion layers avoids these incompatibility problems by giving flexibility in the choice of sol-gels and resulting in more stable and better performing sensors.

In one embodiment, a sensor can comprise a sol-gel and a sol-gel precursor solution comprising a co-polymer and a solvent adapted to resist the deformation of the sol-gel layer. Deformation can be caused by the evaporation of sol-gel precursor, the water content of the sol-gel, the state of condensation of the sol-gel prior to deposition of the sol-gel layer, the rate of continuing condensation, the hydrophilicity of any adhesion layer, additives in the sol-gel, and sensing material in the sol-gel. Shrinking can be the combined result of solvent evaporation and increasing cross-linking of the sol-gel. Cracking can be the result of bulk stress on the material either due to nonuniform shrinking or rapid dehydration of the sol-gel. The term "solvent" refers to any organic solvent, water or other diluent which can comprise additives or other material known in the art to reduce sol-gel deformation.

In one embodiment, deformation can be reduced by treating the matrix prior to sol-gel formation by adding a co-polymer and solvent to the sol-gel components which can decrease the fraction of evaporating components of the sol-gel, decrease the degree of cross-linking in the sol-gel matrix, increase the intermolecular forces in the sol-gel, change the phase of the sol-gel resulting in a more elastic sol-gel layer, or any combination thereof. In another embodiment, the solvent can comprise additives, including but not limited to salts or surfactants such as sodium dodecylsulfate to change the degree of solvent retention or the rate of solvent evaporation.

Deformation can also be reduced by treating the surface of the sol-gel, or by adding mobile material (i.e. one that is free to move throughout the bulk phase of the sol-gel matrix) to the sol-gel or co-attaching or covalently bonding material to the sol-gel matrix (i.e. material that is attached to the sol-gel matrix). In one embodiment, a surface layer can be formed on the sol-gel to reduce the evaporation rate and reduce the free energy on the surface of the sol-gel. In another embodiment of treating the surface of the sol-gel, a surface layer is formed comprising an additive which forms a polymer backbone. An example of treating the surface of the sol-gel with a surface layer results in a surface layer comprising a co-polymer with a long-chain aldehyde that is linked to APES contained in the sol-gel. In a further embodiment, the surface layer can comprise of an additive such as a long alkyl-chain chlorosilane.

In another embodiment, the deformation of the sol-gel layer can be reduced by controlling the deposition characteristics. The term "deposition characteristics" refers to the deposition rate, the type/method of deposition, the shape of the resulting layers as they relate to controlling the uniformity and anisotropy of the condensation rate of the sol-gel thereby controlling the stress on the sol-gel layer as it ages.

In one embodiment, the sensor can comprise of a diffusion control layer, said diffusion control layer comprising at least one barrier to the diffusion of at least one analyte, and a sensing sol-gel layer positioned to receive the analyte diffusing through the diffusion control layer. The term "diffusion control layer" refers to a layer comprising sol-gel or other material that comprises a composition and/or structural barrier for analytes or other materials transported through the layer. The term "varying the barrier" refers to changing the selectivity and an effectiveness of the diffusion control layer for diffusion of analytes through the diffusion control layer. Varying the barrier involves changing sol-gel layer physical properties such as porosity, anisotropy, and thickness, and sol-gel chemical properties such as additives, co-polymers, orthosilicates, catalysts, enzymes, dissolved reagents, and hydrogels.

Varying the barrier involves adjusting the porosity of the diffusion control sol-gel by relative rates of condensation and hydrolysis, the nature of additives and co-polymers, the chemical composition of the orthosilicates in the diffusion control sol-gel, the thickness of the diffusion control layer, the anisotropy in the diffusion control layer between lateral and transverse diffusion rates, the inclusion of catalysts, enzymes, or dissolved reagents, inclusion of additives or copolymers (such as hydrogels) which change the morphology of the diffusion sol-gel layer as a function of analyte concentration, or any combinations thereof. These adjustments can augment or diminish the analyte concentration reaching the underlying sensing sol-gel layer.

An embodiment of an adhesion layer between two sol-gel layers comprises using enzyme glucose oxidase (hereinafter "$GO_x$") to allow crosslinking between a sol-gel with amino functional groups and glutaraldehyde. In one configuration, a layer of sol-gel is adhered to a layer of sol-gel with amino functional groups and with ruthenium(II) trisphenylphenanthroline dichloride (hereinafter "$Ru(DPP)_3Cl_2$") using an adhesion layer of $GO_x$ and glutaraldehyde. In another configuration, a layer of sol-gel with $Ru(DPP)_3Cl_2$ is adhered to a layer of sol-gel with amino functional groups, $GO_x$, and glutaraldehyde without an adhesion layer. In another configuration, a layer of sol-gel with amino functional groups is adhered to a layer of sol-gel with amino functional groups and $Ru(DPP)_3Cl_2$ using an adhesion layer of $GO_x$ and glutaraldehyde. A sol-gel with an amino functional group and $Ru(DPP)_3Cl_2$ is prepared by mixing 0.5 ml of TMOS, 0.25 ml of propyltrimethoxysilane (hereinafter "Pr-Tri-MOS"), 0.25 ml of aminotrimethoxysilane (hereinafter "Amino-Tri-MOS"), 1.25 ml of ethanol, 0.4 ml of one molar hydrochloric acid, and 6.7 mg of $Ru(DPP)_3Cl_2$. APES can be used in lieu of Amino-Tri-MOS, as well as mixtures thereof.

The stability of sol-gel layers depends upon several factors including but not limited to composition (crosslinker to organic modified ratio; silane to water ratio), pH (low pH leads to higher hydrolysis rates; high pH leads to higher condensation rates), temperature, humidity, substrate (whether hydrophobic or hydrophilic; whether cured or uncured), thickness, and morphology. The composition of the sol-gel layer affects microscopic and internal properties of the sol-gel, but has relatively less affect on the mechanical properties of the sol-gel. The pH affects the rate of gel formation and protein stability. Temperature and humidity effects are minimized by varying them gradually throughout gel formation. The substrate is cured to adhere to a sol-gel and adapted to be hydrophilic such that hydrophilic sol-gel layers can attach to its surface. The sol-gel is thin and uniform to provide stability and reduce shrinking and cracking.

An example of an embodiment for the treatment to reduce shrinking and cracking uses a sol-gel comprising 0.5 ml of TMOS, 0.5 ml of propyltrimethoxysilane (hereinafter "Pr-Tri-MOS"), 1.25 ml of ethanol, 0.4 ml of one molar hydrochloric acid, and 6.7 mg of $Ru(DPP)_3Cl_2$. The sol-gel was deposited on different substrates and other sol-gels, treated with plasma or reagents, and stored under dry, humid, or wet conditions, and at room temperature (20° C.) or cold conditions (below 10° C.) to observe whether the sol-gel cracked. Table 1 shows the test conditions for several tests conducted:

TABLE 1

| TEST NUMBER | UNDER SOL-GEL | TREATMENT | STORAGE |
| --- | --- | --- | --- |
| 1 | GLASS | NONE | DRY; ROOM TEMP. |
| 2 | GLASS | NONE | HUMID; ROOM TEMP. |
| 3 | GLASS | NONE | DRY; COLD |
| 4 | GLASS | NONE | HUMID; COLD |
| 5 | SOL-GEL | NONE | DRY; ROOM TEMP. |
| 6 | SOL-GEL | NONE | WET; ROOM TEMP. |
| 7 | SOL-GEL | PLASMA | DRY; ROOM TEMP. |
| 8 | SOL-GEL | PLASMA | WET; ROOM TEMP. |
| 9 | GLASS | WATER | DRY; ROOM TEMP. |
| 10 | GLASS | 0.1 M HCl | DRY; ROOM TEMP. |
| 11 | GLASS | PHOSPHATE BUFFER | DRY; ROOM TEMP. |
| 12 | GLASS | PHOSPHATE BUFFER | HUMID; ROOM TEMP. |
| 13 | PDMS | NONE | DRY; ROOM TEMP. |
| 14 | PDMS | NONE | WET; ROOM TEMP. |
| 15 | PDMS | PLASMA | DRY; ROOM TEMP. |
| 16 | PDMS | PLASMA | WET; ROOM TEMP. |

The sol-gels in Test 4 and Test 12, those stored in humid environments, cracked. The sol-gel became saturated with vapor and during drying the sol-gel released excess precursors. Storage in humid conditions reintroduced water and caused cracking upon drying. Whereas, Test 9 and Test 10, those stored in dry environments, did not show signs of cracking. Rapid dehydration contributes to the cracking.

An example of the embodiment for the treatment of sol-gels to change the chemical nature of the sol-gel surface can be seen in the changes in wettability or water adhesion to the sol-gel surface. A goniometer (Tantek, Inc.) was used to measure water contact angles on sol-gel surfaces as an indication of wettability. The angle within the water phase is known as the water contact angle or wetting angle. It is the angle included between the tangent plane to the surface of the water and the tangent plane to the surface of the sol-gel, at any point along their line of contact.

Sol-gels with different functional groups were prepared for testing. Sol-gels with propyl, methyl, phenyl, and vinyl functional groups were used for the tests. The propyl functional sol-gel was formulated from 0.5 ml of TMOS, 0.405 ml of Pr-Tri-MOS, 1.25 ml of ethanol, and 0.4 ml of one molar hydrochloric acid. The methyl functional sol-gel was formulated from 0.5 ml of TMOS, 0.3371 ml of methyltrimethoxysilane (hereinafter "Me-Tri-MOS"), 1.25 ml of ethanol, and 0.4 ml of one molar hydrochloric acid. The phenyl functional sol-gel was formulated from 0.5 ml of TMOS, 0.640 ml of phenyltrimethoxysilane (hereinafter "Ph-Tri-MOS"), 1.25 ml of ethanol, and 0.4 ml of one molar hydrochloric acid. The vinyl functional sol-gel was formulated from 0.5 ml of TMOS, 0.518 ml of vinyltrimethoxysilane (hereinafter "Pr-Tri-MOS"), 1.25 ml of ethanol, and 0.4 ml of one molar hydrochloric acid.

Once the sol-gels were formed initial water contact angles were measured. Sol-gels were treated with gaseous plasma by exposing the sol-gel for 1.0 minute to the plasma and then the contact angles were measured. Sol-gels were treated with 9 molar $H_2SO_4$ by soaking for 30 seconds and then drying. Sol-gels were treated with dilute $KMnO_4$ by soaking for 15 minutes and then drying. Table 2 shows the results of average water contact angles for tests conducted on the sol-gels with functional groups:

TABLE 2

| GROUP | INITIAL | PLASMA | $H_2SO_4$ | $KmnO_4$ |
| --- | --- | --- | --- | --- |
| METHYL | 84.0 | <5.0 | 45.7 | 72.2 |
| VINYL | 85.3 | <5.0 | 67.0 | 7.0 |
| PROPYL | 98.8 | <5.0 | 71.6 | 77.6 |
| PHENYL | 77.6 | 11.3 | — | — |

The plasma treatment affected the sol-gel surfaces as an example of a general treatment of the sol-gel. As a general treatment, the plasma reduced the contact angles for all four functional sol-gels. The value for the phenyl functional sol-gel was reduced less because of the higher carbon content of the phenyl functional group. Treatment with $H_2SO_4$ and KMnO$_4$ was an example of selective treatment of the sol-gel. As selective treatments, the H$_2$SO$_4$ and KMnO$_4$ had more direct effect on certain functional groups. The H$_2$SO$_4$ reacted with the methyl functional sol-gel, whereas, the KMnO$_4$ reacted with the vinyl functional sol-gel.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A sensor comprising:
   a first sol-gel layer, said sol-gel layer comprising a first functional group;
   a second layer, said second layer comprising a second functional group, wherein said second layer is at least one other layer, wherein said other layer comprises a second sol-gel layer, and a diffusion layer; and
   a linker material connecting said first functional group to said second functional group by one or more covalent bonds.

2. A sensor according to claim 1, wherein;
   said second layer further comprises a substrate.

3. A sensor according to claim 1, wherein:
   said second layer further comprises an adhesion layer, said adhesion layer comprising said linker material; and
   said second layer adhering to at least one other layer, wherein said at least one other layer comprises a second sol-gel layer, a substrate, and a diffusion control layer.

4. A sensor according to claim 3, wherein:
   said first functional group and said second functional group are amino groups.

5. A sensor according to claim 4, wherein:
   said linker material comprises glutaraldehyde.

6. A sensor according to claim 3, wherein:
   said linker material adheres to said first functional group and said second functional group with at least one covalent bond, wherein said one at least one covalent bond is chosen from disulfide bonds, sulfur-metal bonds, and sulfur-peptide bonds.

7. A sensor according to claim 1, wherein:
   said first sol-gel layer comprises a sol-gel precursor, said sot-gel precursor comprises said first functional group, wherein the amount of sol-gel precursor is varied to adjust a sol-gel layer refractive index.

8. A sensor according to claim 1, wherein:
   said first sol-gel layer is adapted for selectivity.

9. A sensor according to claim 8, wherein:
   said selectivity comprises access holes, wherein said access holes are adapted to control penetration into said first sol-gel layer through at least one of size, polarity and chemical affinity.

10. A sensor according to claim 1, further comprising an adhesion layer, wherein
    said linker material is part of the adhesion layer, which is positioned on said second sol-gel layer to at least partially cover said second sol-gel layer, said adhesion layer is adapted to resist the deformation of said first and second sol-gel layers.

11. A sensor according to claim 10, wherein said deformation is chosen from detachment, shrinking, and cracking.

12. A sensor according to claim 1, wherein said second sol-gel layer is at least partially treated with at least one material, wherein said at least one material is chosen from gaseous plasma, gaseous corona, chlorosilane, orthosilicate, glutaraldehyde, additives, and sol-gel precursors of said second sol-gel layer.

13. A sensor according to claim 12, wherein said second sol-gel layer is made from sol-gel precursors adapted to at least one adjustment, wherein said at least one adjustment is chosen from decreasing evaporation, decreasing cross-linking, increasing intermolecular forces, and increasing elasticity.

14. A sensor according to claim 12, wherein:
    said sol-gel precursor further comprises at least one additive, said at least one additive chosen from, a salt, and a surfactant.

15. A sensor according to claim 5, wherein said adhesion layer further comprises glucose oxidase.

16. A sensor according to claim 2, wherein the substrate comprises glass.

17. A sensor according to claim 2, wherein said first sol-gel layer is disposed on top of said substrate, said second sol-gel layer is disposed on top of said first sol-gel layer, and said diffusion layer is disposed on top of said second sol-gel layer.

18. A sensor according to claim 17, wherein an adhesion layer comprising the linker material is disposed between one or more of said substrate and said first sol-gel layer, said first sol-gel layer and said second sol-gel layer, or said second sol-gel layer and said diffusion layer.

19. A sensor according to claim 17, wherein said linker material is diffused throughout one or more of said first sol-gel layer, said second sol-gel layer, and said diffusion layer.

* * * * *

UNITED STATES PATENT AND TRADEMARK OFFICE
CERTIFICATE OF CORRECTION

PATENT NO. : 7,393,693 B2
APPLICATION NO. : 10/159301
DATED : July 1, 2008
INVENTOR(S) : Anvar et al.

It is certified that error appears in the above-identified patent and that said Letters Patent is hereby corrected as shown below:

In column 9, line 44, in Claim 7, delete "sot-gel" and insert -- sol-gel --, therefor.

Signed and Sealed this

Twenty-first Day of October, 2008

JON W. DUDAS
*Director of the United States Patent and Trademark Office*